US010786460B2

(12) United States Patent
Byeon (10) Patent No.: US 10,786,460 B2
(45) Date of Patent: Sep. 29, 2020

(54) PREPARATION APPARATUS FOR NANOCOMPOSITE MATERIAL AND SELF-ASSEMBLY PREPARATION METHOD

(71) Applicant: Research Cooperation Foundation of Yeungnam University, Gyeongsangbuk-do (KR)

(72) Inventor: Jeong Hoon Byeon, Daegu (KR)

(73) Assignee: Research Cooperation Foundation of Yeungnam University, Gyeongsangbuk-do (KR)

(*) Notice: Subject to any disclaimer, the term of this patent is extended or adjusted under 35 U.S.C. 154(b) by 155 days.

(21) Appl. No.: 15/775,063

(22) PCT Filed: Nov. 8, 2016

(86) PCT No.: PCT/KR2016/012789
§ 371 (c)(1),
(2) Date: Sep. 10, 2018

(87) PCT Pub. No.: WO2017/082610
PCT Pub. Date: May 18, 2017

(65) Prior Publication Data
US 2019/0015338 A1 Jan. 17, 2019

(30) Foreign Application Priority Data
Nov. 10, 2015 (KR) .................. 10-2015-0157359

(51) Int. Cl.
*A61K 9/19* (2006.01)
*B01J 13/00* (2006.01)
(Continued)

(52) U.S. Cl.
CPC .......... *A61K 9/1694* (2013.01); *A61K 9/5078* (2013.01); *A61K 9/5192* (2013.01);
(Continued)

(58) Field of Classification Search
None
See application file for complete search history.

(56) References Cited

U.S. PATENT DOCUMENTS

2005/0191491 A1* 9/2005 Wang .................. A61K 9/5089
428/407

FOREIGN PATENT DOCUMENTS

KR 10-2011-0089171 A 8/2011
KR 10-1255149 B1 4/2013
(Continued)

OTHER PUBLICATIONS

J.H. Byeon et al., "Aerosol-processed Thermosensitive Nanocomposites for Controlled Drug Release," ACS Macro Letters, (vol. 3), (p. 369-373), (2014).
(Continued)

*Primary Examiner* — Jeffrey D Washville
(74) *Attorney, Agent, or Firm* — Hammer & Associates, P.C.

(57) ABSTRACT

The present invention relates to a self-assembly preparation method of a nanocomposite material, and more particularly, relates to a self-assembly preparation method of a nanocomposite material comprising steps of: spraying a drug-containing solution onto metal aerosol nano the drug, or the like can be easily controlled through metal types of metal aerosol nanoparticles, modification, and the like.

5 Claims, 3 Drawing Sheets

PREPARATION APPARATUS FOR NANOCOMPOSITE MATERIAL AND SELF-ASSEMBLY PREPARATION METHOD

TECHNICAL FIELD

The present invention relates to a preparation apparatus for a nanocomposite material and a self-assembly preparation method.

BACKGROUND ART

There is an increasing interest in developing an effective system for delivering various therapeutic agents (for example, high molecular weight peptides, proteins and genetic materials, as well as low molecular weight chemical drugs and contrast agents) to specific organs, tissues, cells, cytoplasm, mitochondria, perinuclear regions and nucleus regions. Unlike traditional formulations, position-specific nanotherapeutic agents were designed to maximize bioavailability of the therapeutic agents delivered to target sites, and had low side effects, so that they had been shown to be capable of increasing therapeutic effects while treating diseases. This drug delivery technology is a high value added technology, which increasingly occupies an important part in the overall drug development process and increases its utilization as a method of improving drug compliance and dosing convenience of patients.

Accordingly, as the demand for such nanotherapeutic agents is increasing, various preparation methods are being developed, but they are mostly limited to liquid chemical processes or physicochemical processes under critical operating conditions.

However, in the case of the conventional methods as described above, they must involve a liquid chemical process or a process based on critical conditions, whereby there is a problem that the processes are not only complicated and high cost, but also environmentally unfriendly as harmful components such as waste water and wastes are generated, and there is a limit in continuous processing and processing in a large-area condition.

A nanoparticle complex and a manufacturing method thereof were disclosed in Korean Laid-Open Patent Publication No. 2015-0117503, but no alternative to the above problem was presented.

DISCLOSURE

Technical Problem

It is an object of the present application to provide a preparation apparatus for a nanocomposite material and a self-assembly preparation method, which involve no liquid chemical process, so that the processes are simple and thus can be performed even at a low temperature.

Technical Solution

The present application relates to a preparation apparatus for a nanocomposite material. According to an exemplary preparation apparatus for a nanocomposite material of the present application, it involves no liquid chemical process, so that the processes are simple and can be performed even at a low temperature to suppress deformation of an organic substance or a drug, thereby preparing nanoparticles capable of being used as a drug delivery system and easily controlling a release rate of a drug or the like through metal types of metal aerosol nanoparticles, modification, and the like.

Hereinafter, a preparation apparatus and a preparation method for a nanocomposite material of the present application will be described with reference to the accompanying drawings, and the accompanying drawings are illustrative, where the scope of the preparation apparatus for a nanocomposite material of the present application is not limited by the accompanying drawings.

Figure 1:
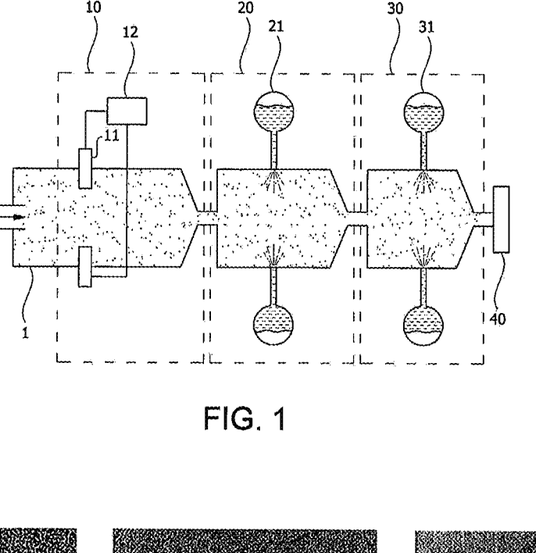
FIG. 1 is a diagram schematically showing a preparation apparatus of the present application.

FIG. 1 is a diagram schematically showing an exemplary preparation apparatus for a nanocomposite material of the present application.

As shown in FIG. 1, the preparation apparatus of the present application comprises a discharge part (10), a first spray part (20), and a second spray part (30).

The discharge part (10) is a part for generating metal nanoparticles by spark discharge, which comprises a pair of conductive rods (11) spaced apart at a predetermined interval and a power supply part (12) for applying a voltage to each of the conductive rods (11).

The pair of conductive rods (11) is spaced apart from each other to form a gap. For example, a spark discharge occurs in the discharge part (10), and metal nanoparticles are generated with a high temperature locally generated between the conductive rods (11) by the spark discharge. The term "gap" or "interval" as used in the present application means a gap between two parts that are moved or fixed, and for example, the interval means a gap between a pair of conductive rods (11) spaced apart, respectively. Also, the term "nano" in the present application is a size in nanometer (nm) units, which may mean, for example, a size of 1 nm to 1000 nm, but is not limited thereto. Furthermore, the term "nanoparticles" in the present application may mean particles having a size in nanometer (nm) units, for example, an average particle diameter of 1 nm to 1000 nm, but is not limited thereto.

A material constituting the conductive rods (11) may include, for example, a transition metal, a transition metal oxide, a transition metal sulfur group element adduct, a lanthanide metal, a lanthanide metal oxide, bismuth, a bismuth sulfur group element adduct, an alloy thereof, and the like. These may be used alone or in a mixture of two or more.

As the transition metal, an element of Group 3 to Group 12 may be used, and gold or silver of these may be preferably used in terms of bio-affinity, antimicrobial activity, photoreactivity and the like.

The transition metal oxide means a metal that a transition metal is oxidized, and the transition metal sulfur group element adduct means a metal that sulfur, selenium, tellurium, or the like of Group 16 is added to a transition metal. If the sulfur group element is added to the transition metal, the nanocomposite material has a fluorescence property, whereby it can be tracked that the nanocomposite material is delivered to the target site within the body and accordingly, it can be determined whether or not the disease is present, or the like.

The lanthanide metal means a metal from lanthanum of atomic number 57 to lutetium of atomic number 71 and the lanthanide metal oxide means a metal that the lanthanide metal is oxidized, where these metals are also used as a contrast agent for MRI or the like, and likewise, it can be tracked that it is delivered to the target site within the body and accordingly, it can be determined whether or not the disease is present, or the like.

The bismuth and bismuth sulfur group element adduct are also used as a contrast agent for CT or the like, and likewise, it can be tracked that it is delivered to the target site within the body and accordingly, it can be determined whether or not the disease is present, or the like.

Also, in the interval between the conductive rods (11), for example, the electrode gap, which is the shortest distance between the conductive rods (11), the shorter the distance is, the lower the ignition required voltage is, and the longer the distance is, the higher voltage is required. Furthermore, if the electrode gap is narrow, the voltage required to generate the spark is reduced, but a short spark can cause misfiring by transmitting the ignition minimum energy to a mixer, so that it is necessary to set an appropriate distance by an experiment. In one example, the gap between the electrodes may be 0.1 to 10 mm or 0.5 to 10 mm, but is not limited thereto.

The power supply part (12) is a part for applying a voltage to each of the conductive rods (11), and in one example, the voltage applied from the power supply part (12) to the conductive rods (11) may be 2 to 5 kV and the amount of current may be from 0.5 to 5 mA, without being limited thereto. For example, the power supply part (12) may control the voltage applied to the pair of conductive rods (11) constantly. Accordingly, metal nanoparticles may be produced with good supply stability by quantitatively supplying metal nanoparticles.

In one example, the power supply part (12) may comprise an electric circuit for applying a high voltage to the conductive rods (11). The electric circuit has a constant voltage source structure composed of a high voltage source (HV), an external capacitor (C) and a resistor (R), which can control the size of the metal nanoparticles using a number of resistors, a number of capacitors and a circuit capable of high speed switching a circuit current.

Although not shown, the apparatus for manufacturing graphene of the present application may comprise a gas supply device such as a carrier gas supply system and a flow meter such as an MFC (mass flow controller). In addition, an inert gas, oxygen or nitrogen can be quantitatively supplied to the interval between the conductive rods by the gas supply device and the flow meter.

When a high voltage is applied to the conductive rods (11), the metal may be vaporized or granulated by the spark discharge and discharged into a first spray part (20) to be described below, along one or more gas flows selected from the group consisting of an inert gas, oxygen and nitrogen flowing through the interval between the conductive rods. For example, when a voltage is applied to the conductive rods (11) of the discharge part (10), the metal is vaporized at the interval between the pair of conductive rods (11) of the discharge part (10), and the vaporized metal moving along the carrier gas such as an inert gas or nitrogen is condensed as it goes out of the interval, thereby forming metal nanoparticles.

In one example, the diameter of the metal aerosol nanoparticles is not particularly limited, which may be, for example, 200 nm or less. When the diameter of the metal aerosol nanoparticles exceeds 200 nm, the intracellular penetration rate may be rapidly lowered. The diameter of the metal aerosol nanoparticles may be preferably 20 nm to 150 nm in view of preventing excessively rapid excretion into the kidney while exhibiting an excellent intracellular penetration rate.

The method of setting the diameter of the metal aerosol nanoparticles in the above range is not particularly limited. For example, when metal aerosol nanoparticles are formed by high heat generated with plasma, it can be performed by a method of varying electric conditions such as voltages, currents and electrode intervals, varying a flow volume, a flow rate, or the like of the carrier gas, or generating electrostatic repulsion between particles through electrostatic unipolar charging, and the like.

For example, the particle diameter of the metal nanoparticles generated from the discharge part (10) may be widely controlled from several nanometer units to hundreds of nanometer units, depending on the flow volume or the flow rate of an inert gas or nitrogen. For example, when the flow volume or the flow rate of the supplied inert gas or nitrogen is increased, an agglomeration phenomenon between the particles also decreases as the concentration of the metal nanoparticles decreases, where the size of nanoparticles may be reduced through this process. Also, the particle diameter, shape and density of the metal nanoparticles may be changed by spark generation conditions such as an applied voltage, a frequency, a current, a resistance and a capacitance value; the type and flow volume of the inert gas; or the shape of the spark electrode, and the like.

The inert gas can be exemplified by argon (Ar) or helium (He), and the like, but is not limited thereto.

The concentration of the metal aerosol nanoparticles generated in the discharge part is not particularly limited, where the nanoparticles may be used, for example, at a number concentration of $10^3$ to $10^{10}/cm^3$. If the number concentration is less than $10^3/cm^3$, the number of metal aerosol nanoparticles is low, so that the process yield is low, whereas if the concentration is more than $10^{10}/cm^3$, the metal aerosol nanoparticles collide with each other, so that there may be a problem that they are agglomerated or attached to the outside rather than the inside of droplets.

The first spray part (20) is a part for forming a drug layer that a drug-containing solution is sprayed on the metal nanoparticles generated in the interval between the conductive rods (11) to surround the metal nanoparticles. When the drug-containing solution is sprayed on the metal aerosol nanoparticles, droplets (small droplets) of the drug-containing solution collide with the metal aerosol nanoparticles and the droplets of the drug-containing solution form the drug layer on the surfaces of the metal aerosol nanoparticles while surrounding the metal aerosol nanoparticles.

As in FIG. 1, the first spray part (20) comprises a drug injector (21) for injecting a drug-containing solution.

In one example, the drug injector (21) may comprise a spray nozzle having an ejection opening. The spray nozzle may be composed of an upper spray nozzle and a lower spray nozzle. The size of the ejection opening of the spray nozzle is not particularly limited, and for example, may have a diameter of 0.05 to 0.5 mm. If the diameter of the nozzle is less than 0.05 mm, the time and cost required for the process can be increased by increasing the clogging frequency of the nozzle, and the process cost can be increased by rapidly increasing the operating pressure. If the diameter of the nozzle exceeds 0.5 mm, the size of the nanocomposite material particles may exceed 200 nm.

In one embodiment, the ejection opening of the nozzle may be one having irregularities on its inner wall. When the irregularities are formed on the inner wall of the ejection opening, the nanocomposite material having a more uniform particle diameter can be prepared by reducing particle diameter distribution of the droplets.

In the first spray part (20), the drug-containing solution is sprayed into the spray part (20) through the spray nozzle (20) in the form of droplets, whereby the metal aerosol nanoparticles generated in the discharge part (10) may be encapsulated by the droplets.

The drug contained in the drug-containing solution may include, for example, an anticancer agent such as doxorubicin and taxol, and various bio-functional approval formulations may also be used without limitation. These may be used alone or in a mixture of two or more.

The solvent contained in the drug-containing solution may include, for example, water, an alcohol having 1 to 6 carbon atoms, or the like, which may further comprise a dispersion accelerator, such as polyvinyl alcohol (PVA), polypyrrolidone (PVP) and polyaniline (PA), for accelerating drug dispersion. In addition, it may further comprise a substance, such as poly-L-lysine (PLL), chitosan and polyethyleneimine, which can be used as a targeting agent.

The concentration of the drug in the drug-containing solution is not particularly limited, which may be used, for example, in an amount of 0.01 to 10% by volume. If the concentration of the drug is less than 0.01% by volume, it is difficult to achieve a drug filling rate of 0.1% or more, so that drug efficacy is insufficient, or excessive amounts of the drug must be ingested in order to exhibit sufficient drug efficacy. If the concentration of the drug is more than 10% by volume, the outer coating of the drug may become incomplete or the size of the metal aerosol nanoparticles on which the drug layer is formed may exceed 200 nm.

As in FIG. 1, the second spray part (30) comprises a polymer injector (31) for injecting a polymer-containing solution.

In one example, the polymer injector (31) may comprise a spray nozzle having an ejection opening. The spray nozzle may be composed of an upper spray nozzle and a lower spray nozzle. The size of the ejection opening of the spray nozzle is not particularly limited, and for example, may have a diameter of 0.05 to 0.5 mm. If the diameter of the nozzle is less than 0.05 mm, the time and cost required for the process can be increased by increasing the clogging frequency of the nozzle, and the process cost can be increased by rapidly increasing the operating pressure. If the diameter of the nozzle exceeds 0.5 mm, the size of the nanocomposite material particles may exceed 200 nm.

In one embodiment, the ejection opening of the nozzle may be one having irregularities on its inner wall. When the irregularities are formed on the inner wall of the ejection opening, the nanocomposite material having a more uniform particle diameter can be prepared by reducing particle diameter distribution of the droplets.

In the second spray part (30), the polymer-containing solution is sprayed into the second spray part (30) through the spray nozzle in the form of droplets, whereby the metal aerosol nanoparticles, on which the drug layer generated in the first spray part (20) is formed, may be encapsulated by the droplets.

The polymer contained in the polymer-containing solution is a biodegradable polymer, which may include, for example, a bio-affinity organic material such as poly-N-isopropylacrylamide (PNIPAM), polydimethylsiloxane, poly-L-lysine (PLL), polylactic acid (PLA), poly(lactic-co-glycolic acid) (PLGA) and chitosan, and biodegradable polymers known in the art may also be used. These may be used alone or in a mixture of two or more.

The solvent contained in the polymer-containing solution may include, for example, water, an alcohol having 1 to 6 carbon atoms, or the like, which may further comprise a dispersion accelerator, such as polyvinyl alcohol (PVA), polypyrrolidone (PVP) and chitosan, for accelerating polymer dispersion.

The concentration of the polymer in the polymer-containing solution is not particularly limited, which may be used, for example, in an amount of 0.01 to 10% by volume. If the concentration of the polymer is less than 0.01% by volume, it may be difficult to form the polymer layer, whereas if the concentration of the polymer is more than 10% by volume, the particle size of the nanocomposite material may exceed 200 nm and the thickness of the polymer layer becomes thicker, so that it may be difficult for the drug to be sufficiently released to the outside of the polymer layer.

In one example, the nozzle of the first spray part and the nozzle of the second spray part may be charged with different electric charges.

Accordingly, the drug-containing solution and the polymer-containing solution may be sprayed through the nozzles charged with different electric charges. In such a case, the drug-containing solution and the polymer-containing solution are charged so as to exhibit different electric charges, so that as the droplets of the polymer-containing solution exhibit repulsion with each other but exhibit electric attraction with the drug layer, the polymer layer may be formed at a higher yield and the nanocomposite material having a more uniform size may be formed.

The present application also relates to a self-assembly preparation method of the above-described nanocomposite material. An exemplary preparation method of the present application comprises steps of spraying a drug-containing solution onto metal aerosol nanoparticles to form a drug layer on the metal aerosol nanoparticles; and spraying a polymer-containing solution onto the metal aerosol nanoparticles, on which the drug layer is formed, to form a polymer layer on the drug layer, whereby since the method involves no liquid chemical process upon producing the metal aerosol nanoparticles, the processes are simple and can be performed even at a low temperature to suppress deformation of an organic or a drug, and the release rate of the drug, or the like can be easily controlled through metal types of metal aerosol nanoparticles, modification, and the like.

One embodiment of the self-assembly preparation method of a nanocomposite material of the present application comprises a step of first spraying a drug-containing solution on metal aerosol nanoparticles to form a drug layer on the metal aerosol nanoparticles.

When the drug-containing solution is sprayed on the metal aerosol nanoparticles, droplets (small droplets) of the drug-containing solution collide with the metal aerosol nanoparticles and the droplets of the drug-containing solution form the drug layer on the surfaces of the metal aerosol nanoparticles while surrounding the metal aerosol nanoparticles.

The metal forming the metal aerosol nanoparticles may include, for example, a transition metal, a transition metal oxide, a transition metal sulfur group element adduct, a lanthanide metal, a lanthanide metal oxide, bismuth, a bismuth sulfur group element adduct, an alloy thereof, and the like. These may be used alone or in a mixture of two or more.

As the transition metal, an element of Group 3 to Group 12 may be used, and gold or silver of these may be preferably used in terms of bio-affinity, antimicrobial activity, photoreactivity and the like.

The transition metal oxide means a metal that a transition metal is oxidized, and the transition metal sulfur group element adduct means a metal that sulfur, selenium, tellurium, or the like of Group 16 is added to a transition metal. If the sulfur group element is added to the transition metal, the nanocomposite material has a fluorescence property, whereby it can be tracked that the nanocomposite material is delivered to the target site within the body and accordingly, it can be determined whether or not the disease is present, or the like.

The lanthanide metal means a metal from lanthanum of atomic number 57 to lutetium of atomic number 71 and the lanthanide metal oxide means a metal that the lanthanide metal is oxidized, where these metals are also used as a contrast agent for MRI or the like, and likewise, it can be tracked that it is delivered to the target site within the body and accordingly, it can be determined whether or not the disease is present, or the like.

The bismuth and bismuth sulfur group element adduct are also used as a contrast agent for CT or the like, and likewise, it can be tracked that it is delivered to the target site within the body and accordingly, it can be determined whether or not the disease is present, or the like.

The diameter of the metal aerosol nanoparticles is not particularly limited, which may be, for example, 200 nm or less. When the diameter of the metal aerosol nanoparticles exceeds 200 nm, the intracellular penetration rate may be rapidly lowered. The diameter of the metal aerosol nanoparticles may be preferably 20 nm to 150 nm in terms of preventing excessively rapid excretion into the kidney while exhibiting an excellent intracellular penetration rate.

The method of controlling the diameter of the metal aerosol nanoparticles in the above-described range is not particularly limited. For example, when metal aerosol nanoparticles are formed by high heat generated with plasma, it can be controlled by a method of varying electric conditions such as voltages, currents and electrode intervals, varying a flow volume, a flow rate, or the like, or generating electrostatic repulsion between particles through electrostatic unipolar charging, and the like.

The concentration of the metal aerosol nanoparticles is not particularly limited, where the nanoparticles may be used, for example, at a number concentration of $10^3$ to $10^{10}/cm^3$. If the number concentration is less than $10^3/cm^3$, the number of metal aerosol nanoparticles is low, so that the process yield is low, whereas if the concentration is more than $10^{10}/cm^3$, the metal aerosol nanoparticles collide with each other, so that there may be a problem that they are agglomerated or attached to the outside rather than the inside of droplets.

In the preparation method of the present application, the metal aerosol nanoparticles may be dispersed in nitrogen or an inert gas. Since the nitrogen or inert gas has low reactivity and is stable, it is possible to form the drug layer and a polymer layer to be described below more stably without side reactions. Furthermore, the metal aerosol nanoparticles may also be dispersed in a gas containing oxygen.

The inert gas may include, for example, helium, argon or the like, which may be used alone or in a mixture of two or more.

In addition, the metal aerosol nanoparticles may be moved along the flow of the carrier gas. In such a case, the metal aerosol nanoparticles can contact the drug-containing solution and the polymer-containing solution while continuously moving, so that agglomeration between the metal aerosol nanoparticles, agglomeration between the drug-containing solutions, agglomeration between the polymer-containing solutions, and agglomeration between the metal aerosol nanoparticles formed only up to the drug layer can be suppressed.

The carrier gas may be, for example, nitrogen, oxygen, an inert gas or the like, which may be used alone or in a mixture of two or more. In the case of the nitrogen or inert gas, it has low reactivity, so that the generation of by-products can be suppressed. When the metal forming the metal aerosol nanoparticles is a metal of oxide, the carrier gas may comprise oxygen.

The carrier gas may be a gas at normal temperature and normal pressure.

The drug contained in the drug-containing solution may include, for example, an anticancer agent such as doxorubicin and taxol, and various bio-functional approval formulations may also be used without limitation. These may be used alone or in a mixture of two or more.

The solvent contained in the drug-containing solution may include, for example, water, an alcohol having 1 to 6 carbon atoms, or the like, which may further comprise a dispersion accelerator, such as polyvinyl alcohol (PVA), polypyrrolidone (PVP) and polyaniline (PA), for accelerating drug dispersion. In addition, it may further comprise a substance, such as poly-L-lysine (PLL), chitosan and polyethyleneimine, which can be used as a targeting agent.

The concentration of the drug in the drug-containing solution is not particularly limited, which may be used, for example, in an amount of 0.01 to 10% by volume. If the concentration of the drug is less than 0.01% by volume, it is difficult to achieve a drug filling rate of 0.1% or more, so that drug efficacy is insufficient, or excessive amounts of the drug must be ingested in order to exhibit sufficient drug efficacy. If the concentration of the drug is more than 10% by volume, the outer coating of the drug may become incomplete or the size of the metal aerosol nanoparticles on which the drug layer is formed may exceed 200 nm.

The drug-containing solution may be sprayed through a nozzle.

The size of the ejection opening of the nozzle is not particularly limited, and for example, may have a diameter of 0.05 to 0.5 mm. If the diameter of the nozzle is less than 0.05 mm, the time and cost required for the process can be increased by increasing the clogging frequency of the nozzle, and the process cost can be increased by rapidly increasing the operating pressure. If the diameter of the nozzle exceeds 0.5 mm, the size of the nanocomposite material particles may exceed 200 nm.

The ejection opening of the nozzle may be one having irregularities on its inner wall. In such a case, the nanocomposite material having a more uniform particle diameter can be prepared by reducing particle diameter distribution of the droplets.

The preparation method of the present application may further comprise a step of forming metal aerosol nanoparticles before the step of forming the drug layer.

The method of forming the metal aerosol nanoparticles is not particularly limited, and for example, they may be formed by a method of vaporizing a metal component by high heat generated with plasma to form them, a method of heating a metal raw material with high heat, a method of spraying a solution containing a metal reagent solution in an ionic state, and the like.

In the case of the method of vaporizing a metal component by high heat generated with plasma to form metal aerosol nanoparticles, the plasma is generated when a high voltage is applied to both metal electrodes and the metal component of the metal electrodes is vaporized by high heat generated with the plasma and then condensed, whereby the metal aerosol nanoparticles can be formed.

At this time, the interval between both metal electrodes may be in a range of 0.5 mm to 10 mm. For example, when the interval between the metal electrodes is 1 mm, the metal component of the metal electrodes may be vaporized to form the metal aerosol nanoparticles, while high heat of 5000° C.

or so is generated in the plasma channel upon applying a high voltage of 2.5 kV to 3 kV. They may be produced by condensing the vaporized metal aerosol nanoparticles by a rapidly lowered environmental temperature during the movement of the vaporized metal aerosol nanoparticles to the plasma outer region having a lower temperature than the plasma generation point.

The high voltage power source applied to the metal electrodes may be a direct current or an alternate current, where in the case of an alternate current, the power application examples such as square waves, triangular waves and offset control may be more various.

In the case of the method of heating a metal raw material with high heat, the metal component may be vaporized by heating the metal raw material with high heat of, for example, 500° C. to 2,000° C., and then condensed to form the metal aerosol nanoparticles.

The heating of the metal for forming the metal aerosol nanoparticles is preferably performed through local heating in order to inhibit thermal damage of the drug or polymer to be described below.

In the case of the method of spraying a solution containing a metal reagent solution in an ionic state, the metal reagent solution may be injected into a solvent and then sprayed thereon, heated to a temperature of, for example, 40 to 200° C. and vaporized and then, condensed to form the metal aerosol nanoparticles.

As the metal reagent solution, the above-described metal reagent solution may be used, and in the case of the transition metal, for example, a transition metal precursor such as $KAu(CN)_2$ and $AgNO_3$ may be used, but is not limited thereto, where all the precursors of the above-described metals may be used.

The solvent used in the preparation of the metal reagent solution may include, for example, water, an alcohol having 1 to 6 carbon atoms, or the like.

According to such a method, as the metal aerosol nanoparticles are produced by the dry method in the aerosol state, there is no problem such as generation of wastewater or wastes as in the prior art, so that it is environment-friendly, and it is possible to perform continuous processes, so that speeding up of the processes is possible.

In addition, the preparation method of the present application may further comprise a step of diluting the metal aerosol nanoparticles after formation of the drug layer. If the metal aerosol nanoparticles are further diluted, the agglomeration of the metal aerosol nanoparticles, on which the drug layer is formed, is suppressed, whereby the production yield of the metal aerosol nanoparticles formed up to the polymer layer to be described below may be further improved.

The step of diluting the metal aerosol nanoparticles can be performed by further increasing the amount of gas in the system in which the metal aerosol nanoparticles are dispersed. That is, when the metal aerosol nanoparticles are dispersed in the gas, it can be performed by increasing the amount of the gas, and when the metal aerosol nanoparticles move along the flow of the carrier gas, it can be performed by increasing the amount of the carrier gas.

The dilution magnification of the metal aerosol nanoparticles is not particularly limited, and for example, they may be diluted 3 to 8 times. If the dilution magnification is less than 3 times, the agglomeration inhibitory effect by dilution may be insignificant, whereas if the dilution magnification is more than 8 times, they are excessively diluted, so that the formation yield of the polymer layer may be then lowered.

In addition, the metal aerosol nanoparticles may be treated with ultraviolet rays. The ultraviolet rays may have a wavelength of, for example, 180 to 365 nm. If the metal aerosol nanoparticles are treated with ultraviolet rays, it is possible to continuously control surface properties (zeta potential, etc.) and shapes of the produced nanoparticles.

Thereafter, the polymer-containing solution is sprayed onto the metal aerosol nanoparticles, on which the drug layer is formed, to form a polymer layer on the drug layer.

The polymer contained in the polymer-containing solution is a biodegradable polymer, which may include, for example, a bio-affinity organic material such as poly-N-isopropylacrylamide (PNIPAM), polydimethylsiloxane, poly-L-lysine (PLL), polylactic acid (PLA), poly(lactic-co-glycolic acid) (PLGA) and chitosan, and biodegradable polymers known in the art may also be used. These may be used alone or in a mixture of two or more.

The solvent contained in the polymer-containing solution may include, for example, water, an alcohol having 1 to 6 carbon atoms, or the like, which may further comprise a dispersion accelerator, such as polyvinyl alcohol (PVA), polypyrrolidone (PVP) and chitosan, for accelerating polymer dispersion.

The concentration of the polymer in the polymer-containing solution is not particularly limited, which may be used, for example, in an amount of 0.01 to 10% by volume. If the concentration of the polymer is less than 0.01% by volume, it may be difficult to form the polymer layer, whereas if the concentration of the polymer is more than 10% by volume, the particle size of the nanocomposite material may exceed 200 nm and the thickness of the polymer layer becomes thicker, so that it may be difficult for the drug to be sufficiently released to the outside of the polymer layer.

The polymer-containing solution may be sprayed in the same manner as the aforementioned drug-containing solution. In such a case, the above-described advantages can be equally represented.

In the preparation method of the present application, the drug-containing solution and the polymer-containing solution may be sprayed through the nozzles charged with different electric charges. In such a case, the drug-containing solution and the polymer-containing solution are charged so as to exhibit different electric charges, so that as the droplets of the polymer-containing solution exhibit repulsion with each other but exhibit electric attraction with the drug layer, the polymer layer may be formed at a higher yield and the nanocomposite material having a more uniform size may be formed.

In addition, the metal aerosol nanoparticles may also be charged to have electric charges different from those of the drug-containing solution. In such a case, likewise, the metal aerosol nanoparticles exhibit attraction with the drug-containing solution, so that the drug layer may be formed at a higher yield.

The self-assembly preparation method of a nanocomposite material of the present application may further comprise a step of drying the drug layer after formation of the drug layer, and a step of drying the polymer layer after formation of the polymer layer.

The solvent of the drug layer and the solvent of the polymer layer can be removed by drying. The drying condition is not particularly limited, and for example, the drying may be performed at 40° C. to 200° C. in terms of suppressing damage of the drug.

According to the preparation method of a nanocomposite material of the present application, a nanocomposite material, in which a drug layer and a polymer layer are sequentially laminated on metal nanoparticle cores, can be obtained. Since the drug layer is protected by the polymer layer, the drug can be efficiently delivered to the target site by a method of controlling the material and thickness of the polymer layer, or the like. In addition, since the metal nanoparticle cores are present, the drugs can be easily controlled as sustained release, immediate release and exothermic drugs by controlling the release time of the drugs through modification such as change of the types of metal or irradiation with ultraviolet rays.

Advantageous Effects

Since the self-assembly preparation method of a nanocomposite material of the present application involves no liquid chemical process upon producing the metal aerosol nanoparticles, the processes are simple. Accordingly, it can be performed even at a low temperature to suppress deformation of an organic substance or a drug, thereby preparing nanoparticles capable of being used as a drug delivery system, and in addition, according to the preparation method of a nanocomposite material of the present application, it can easily control a release rate of a drug or the like through metal types of metal aerosol nanoparticles, modification, and the like.

BEST MODE

Hereinafter, the above-described contents will be described in more detail through Examples and Comparative Examples, but the scope of the present application is not limited by the following contents.

Example 1

Figure 2:
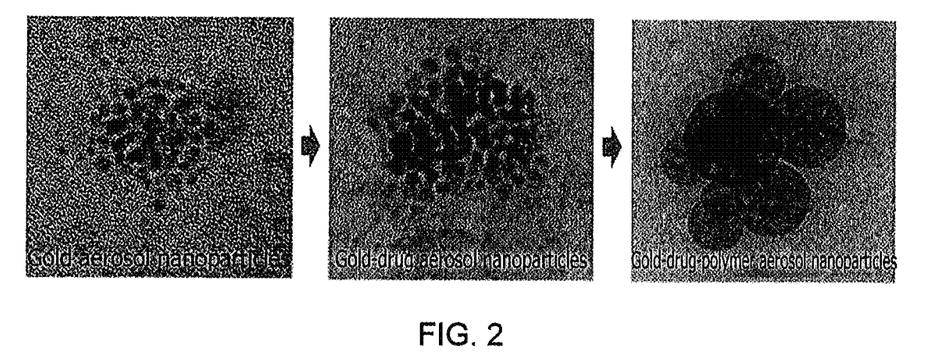
FIG. 2 is photographs of processes that a nanocomposite material is formed according to a preparation method of the present application.

Using the apparatus of FIG. 1, a nanocomposite material was produced by the procedure shown in FIG. 2.
1. Preparation of Metal Aerosol Nanoparticles
A voltage of the following conditions was applied to a spark generator of the following specifications to generate metal vapor, and the vapor was condensed outside the spark generation point to obtain metal aerosol nanoparticles.
<Spark Generator Specifications and Conditions>
Positive electrode: Au
Negative electrode: Fe—Pt
Electrode diameter: 3 mm
Electrode length: 100 mm
Resistance: 0.5 MΩ
Capacitance: 1.0 nF
Load current: 2.0 mA
Applied voltage: 3 kV
Frequency: 1 kHz
2. Formation of Drug Layer
A nitrogen gas (99.99999%>) was supplied between both the metal electrodes to move the metal aerosol nanoparticles along the flow of nitrogen. The flow rate of nitrogen was set to 1.0 to 5.0 L/min, and the number concentration of the metal aerosol nanoparticles was $10^4$ to $10^8/cm^3$.

A drug-containing solution was sprayed onto the metal aerosol nanoparticles moving along the flow of nitrogen.

The drug-containing solution was prepared by dissolving doxorubicin in a solvent, and the concentration of the drug was adjusted to 0.01 to 10% by volume.

The spraying was performed through a nozzle having a 0.3 mm diameter ejection opening.

Then, the drug layer was dried by passing the metal aerosol nanoparticles, on which the drug layer was formed, through a heat pipe near 100° C.

3. Formation of Polymer Layer
Prior to formation of a polymer layer, the flow rate of nitrogen as the carrier gas was increased 5 times to dilute the metal aerosol nanoparticles on which the drug layer was formed.

A polymer-containing solution was sprayed onto the metal aerosol nanoparticles, on which the drug layer was formed, moving along the flow of nitrogen.

The polymer-containing solution was prepared by dissolving polyethyleneimine in a solvent, and the concentration of the polymer was adjusted to 0.1 to 10% by volume.

The spraying was performed through a nozzle having a 0.3 mm diameter ejection opening.

Then, the polymer layer was dried by passing the metal aerosol nanoparticles, on which the polymer layer was formed, through a heat pipe near 100° C.

Example 2

Using the apparatus of FIG. 1, a nanocomposite material was produced by the procedure shown in FIG. 2.

Metal vapor was produced by a spark generator (manufactured by inventors themselves), and the vapor was condensed outside the spark generation point to obtain gold aerosol nanoparticles. Specifically, the spark generation operating conditions was set at an interval of 1 mm between the gold electrodes, an operating voltage of 3 kV and a current of 4.1 mA. The spark frequency was controlled by applying a capacitor of 1 nF and the gold electrode vaporized by the high temperature spark channel was condensed along the nitrogen gas flow to produce gold aerosol nanoparticles. The particle diameters of the prepared gold aerosol nanoparticles were measured by a scanning mobility particle sizer (SMPS) provided with an electrostatic classifier (3085, TSI, USA), a condensation particle counter (3776, TSI, USA) and an aerosol charge neutralizer (4530, HCT, Korea), and the measured particle diameters were 4 to 200 nm. Nitrogen gas (>99.99999% purity) was supplied between the gold electrodes to move the gold aerosol nanoparticles along the flow of nitrogen. The flow rate of nitrogen was 3.0 L/min and the number concentration of gold aerosol nanoparticles was $3.2 \times 10^7/cm^3$.

To produce uniform sized gold-triton aggregates using a collision atomizer (containing 2.5 v/v % Triton X-100 and 0.1 w/v % doxorubicin), gold aerosol nanoparticles were first prepared through the spark generator in the compressed nitrogen gas and then the nitrogen gas that the prepared gold aerosol nanoparticles floated was used as a working fluid for the collision atomizer. The collision atomizer was operated at a fluid pressure of 0.25 MPa, the total diameter of the nozzles was 0.3 mm, and an orifice having a plurality of projections with a diameter of 0.05 mm was mounted on the inner wall surface of the nozzle. The solution containing gold aerosol nanoparticles in the collision atomizer passed through the nozzle, to which irregularities were applied, to be uniformly subjected to droplets and then dried, where the uniform sized nanocomposite material was produced.

Thereafter, a drug-containing solution was sprayed onto the gold aerosol nanoparticles moving along the flow of nitrogen. The drug-containing solution was prepared by dissolving 2.5 v/v % Triton X-100 and 0.1 w/v % doxorubicin in a hexane solvent, where the drug concentration was controlled by changing the relative ratio of doxorubicin. The drug-containing solution was sprayed with the nozzle to which irregularities were applied. The total diameter of the nozzle was 0.3 mm, and the inner wall surface of the nozzle included a plurality of protrusions having a diameter of 0.05 mm. The irregularities were electrostatically positively charged at an intensity of 2.7 kV/cm to have electrical repulsion between droplets. As the drug-containing solution collided with the first prepared gold aerosol nanoparticles at the nozzle portion, the gold aerosol nanoparticles were encapsulated by the drug-containing solution and passed through a heat pipe near 100° C. to vaporize the solvent component in the drug solution.

Figure 3:
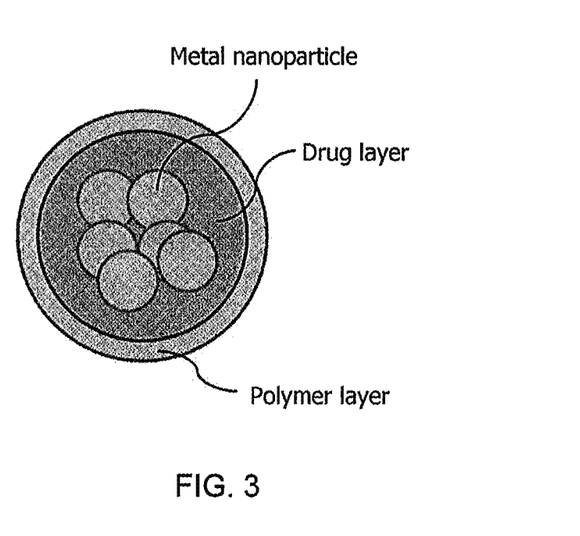
FIG. 3 is a diagram schematically showing a cross-section of a nanocomposite material produced according to a preparation method of the present application.

To add targeting ability of the prepared particles to biological tissues, a cationic polymer-containing solution was sprayed onto the gold aerosol nanoparticles, on which the drug layer was formed, moving along the flow of nitrogen. The polymer-containing solution was prepared by dissolving polyethyleneimine in an ethanol solvent, where the concentration of the polymer was adjusted to 0.1 v/v %. The polymer-containing solution was sprayed with a nozzle having the same specification as that of the nozzle used in the drug-containing solution, and the irregularities were also electrostatically positively charged at an intensity of 2.7 kV/cm to have electrical repulsion between the droplets, where size uniformity by agglomeration between the droplets was maintained. As the droplets of the polymer-containing solution collided with the gold aerosol nanoparticles on which the drug layer was formed, the drug layer was encapsulated by the polymer-containing layer and passed through a heat pipe near 100° C. to vaporize the solvent, whereby a nancomposite material having a multi-layered structure (layer-by-layer) was prepared as shown in FIG. 3.

Comparative Example

A nanocomposite material was prepared in the same manner as in Example 2 except that irregularities were not formed on the inner wall of the nozzle.

Experimental Example—Particle Diameter Measuring Method and Result Analysis

Figure 4:
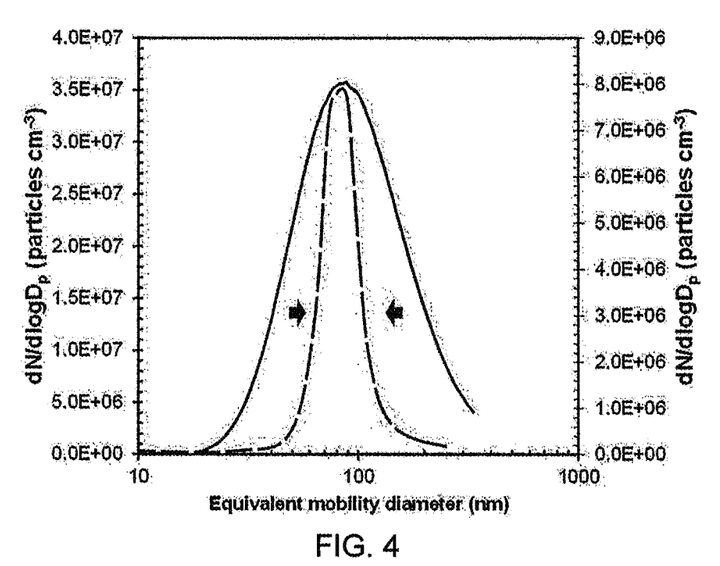
FIG. 4 is a graph of the results that the particle diameters of the nanocomposite materials of Example 2 and Comparative Example are measured by a scanning mobility particle sizer in a gas phase.
Figure 5:
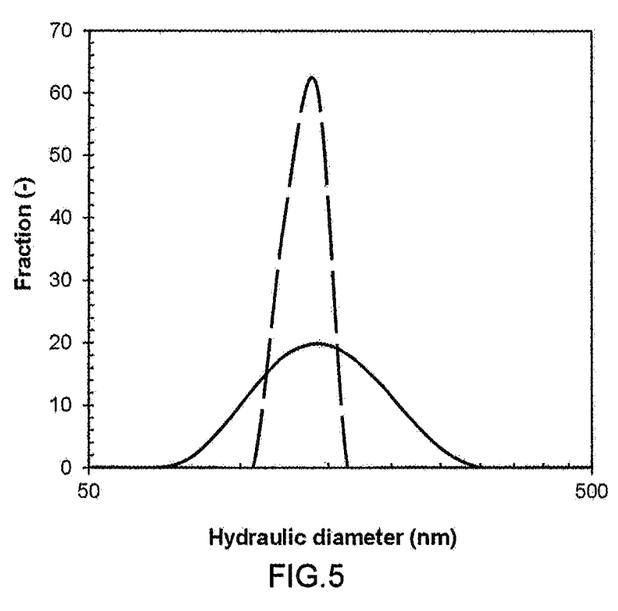
FIG. 5 is a graph of the results that the particle diameters of the nanocomposite materials of Example 2 and Comparative Example are measured by a dynamic light scattering particle sizer (Nano ZS90, Malvern Instruments, UK) in a liquid phase.

The particle diameters of the nanocomposite materials of Example 2 and Comparative Example were measured with a scanning mobility particle sizer in the gas phase and with a dynamic light scattering particle sizer (Nano ZS90, Malvern Instruments, UK) in the liquid phase, and the results were shown in FIGS. 4 and 5, respectively.

As shown in FIG. 4, from the scanning mobility particle sizer measurement results, in the case of Comparative Example (solid line), the particle size distribution was not uniform and the width was very wide, but in the case of Example 2 (dotted line), the particle size distribution became remarkably uniform.

Also, as shown in FIG. 5, from the dynamic scattering particle sizer measurement results, in the case of Comparative Example (solid line), the particle size distribution was not uniform and the width was very wide, but in the case of Example 2 (dotted line), the particle size distribution was remarkably uniform.

As the irregularities are applied to the nozzle, this is because the physical conditions applied to the droplets passing through the nozzle are made uniform.

The invention claimed is:

1. A preparation apparatus for a nanocomposite material comprising:
   a discharge part which comprises a pair of conductive rods spaced apart at a predetermined interval to form an interval and containing a metal, and a power supply part for applying a voltage to the conductive rods, wherein metal nanoparticles are generated at the interval between the conductive rods by spark discharge;
   a first spray part which comprises a drug injector for injecting a drug-containing solution onto the metal nanoparticles generated in the interval between the conductive rods, and forms a drug layer surrounding the metal nanoparticles; and
   a second spray part which comprises a polymer injector for injecting a polymer-containing solution onto the metal nanoparticles on which the drug layer is formed, and forms a polymer layer surrounding the drug layer,
   wherein the drug injector and the polymer injector comprise a nozzle having an ejection opening,
   wherein the nozzle of the first spray part and the nozzle of the second spray part are charged with different electric charges.

2. The preparation apparatus for a nanocomposite material according to claim 1, wherein the metal is one or more selected from the group consisting of a transition metal, a transition metal oxide, a transition metal sulfur group element adduct, a lanthanide metal, a lanthanide metal oxide, bismuth, a bismuth sulfur group element adduct and an alloy thereof.

3. The preparation apparatus for a nanocomposite material according to claim 1, wherein the discharge part, the first spray part and the second spray part are maintained under one or more carrier gas atmospheres selected from the group consisting of nitrogen, an inert gas and oxygen.

4. The preparation apparatus for a nanocomposite material according to claim 1, wherein the ejection opening has irregularities on its inner wall.

5. The preparation apparatus for a nanocomposite material according to claim 1, wherein the ejection opening has a diameter of 0.05 mm to 0.5 mm.

* * * * *